(12) United States Patent
Jablow

(10) Patent No.: US 8,795,636 B2
(45) Date of Patent: Aug. 5, 2014

(54) TOOTH WHITENER AND MAINTENANCE WITH BLEACH BUMPERS

(75) Inventor: Jennifer Jablow, New York, NY (US)

(73) Assignee: Jasibo, LLC., Las Vegas, NV (US)

( * ) Notice: Subject to any disclaimer, the term of this patent is extended or adjusted under 35 U.S.C. 154(b) by 1407 days.

(21) Appl. No.: 11/985,944

(22) Filed: Nov. 19, 2007

(65) Prior Publication Data
US 2008/0181855 A1    Jul. 31, 2008

Related U.S. Application Data

(60) Provisional application No. 60/859,644, filed on Nov. 17, 2006, provisional application No. 60/994,866, filed on Sep. 21, 2007.

(51) Int. Cl.
| | | |
|---|---|---|
| *A61K 6/00* | (2006.01) | |
| *A61Q 11/00* | (2006.01) | |
| *A61C 3/00* | (2006.01) | |
| *A61C 5/14* | (2006.01) | |
| *A61K 8/66* | (2006.01) | |
| *A61K 8/34* | (2006.01) | |
| *A61K 8/25* | (2006.01) | |
| *A61K 8/81* | (2006.01) | |
| *A61K 8/22* | (2006.01) | |
| *A61C 19/06* | (2006.01) | |
| *A61K 8/04* | (2006.01) | |

(52) U.S. Cl.
CPC ............... *A61C 5/14* (2013.01); *A61K 2800/88* (2013.01); *A61K 8/66* (2013.01); *A61K 8/345* (2013.01); *A61K 8/25* (2013.01); *A61Q 11/00* (2013.01); *A61K 8/8176* (2013.01); *A61K 8/22* (2013.01); *A61C 19/066* (2013.01); *A61K 8/042* (2013.01); *A61K 8/34* (2013.01)
USPC ............................. 424/49; 433/140; 433/215

(58) Field of Classification Search
USPC .................................... 424/49; 433/140, 215
See application file for complete search history.

(56) References Cited

U.S. PATENT DOCUMENTS

| | | | | |
|---|---|---|---|---|
| 4,705,514 A | * | 11/1987 | Barnard ........................ | 604/383 |
| 6,305,936 B1 | * | 10/2001 | Jensen et al. ................. | 433/136 |
| 2003/0211056 A1 | * | 11/2003 | Sagel et al. .................... | 424/53 |
| 2005/0026103 A1 | * | 2/2005 | Wasylucha ..................... | 433/29 |

OTHER PUBLICATIONS

Dentist.net. Rembrandt Dazzling White Superior Mouthguard Bleaching. Jan. 15, 2004.*
Omnia, Inc. Dental Rolls. Jun. 18, 2006.*
Colgate-Palmolive-Peet Company. GB741315A. Nov. 30, 1955.*

* cited by examiner

*Primary Examiner* — Frederick Krass
*Assistant Examiner* — Tracy Liu
(74) *Attorney, Agent, or Firm* — Ziegler IP Law Group, LLC

(57) ABSTRACT

A tooth whitening and maintenance system and method and a system and method for protecting the gums.

9 Claims, 1 Drawing Sheet

TOOTH WHITENER AND MAINTENANCE WITH BLEACH BUMPERS

RELATED APPLICATIONS

This application claims priority to provisional patent application Ser. No. 60/859,644 filed Nov. 17, 2006 and provisional patent application Ser. No. 60/994,866 filed Sep. 21, 2007.

FIELD OF THE INVENTION

The present invention relates to a tooth whitening system and method and a system and method for protecting the gums.

BACKGROUND OF THE INVENTION

U.S. Pat. No. 6,305,936 relates to polymerizable dental isolation barriers having a monomer and an initiator.

U.S. Pat. No. 5,499,917 relates to a dental isolation dam having a plurality of elastic fibers arranged in a rectangular, crisscrossed pattern between impervious films. The fibers enable the dam to be easily placed and clinch around necks of isolated teeth.

U.S. Pat. No. 7,157,502 relates to a polymerizable dental barrier material and method of making the same. The material is used for isolating dental tissues during dental procedures.

U.S. Patent pub. no. 2004/0219486 relates to a rubber dam comprising a barrier membrane, an operative insert engaged to the sheet of barrier material and an integrally attached exterior frame to enable a dentist to isolate various portions of the dental alveolar arch.

U.S. Patent pub. no. 2004/0170945 relates to an isolation rubber dam composed of an elastic membrane with a slit-like central opening through which a grouping of teeth and their soft tissues are brought into the dental operative field.

U.S. Patent pub. nos. 2003/0190584 and 2006/0177796 relate to an isolation rubber dam having an operative insert in the form of a wire which is embedded in or applied to a sheet of elastomeric material.

U.S. Patent pub. no. 2006/0069316 and 2006/0063979 relate to a retracting device for retracting at least a portion of a users mouth.

U.S. Patent pub. no. 2005/0017407 relates to a mold shim or insert which is placed between the surface of a forming mold or mold magnet and a fastener strip that has to be molded into a foam object.

U.S. Patent pub. no. 2005/0266378 relates to two and three dimensional rubber dams.

There are many paint on or brush on tooth whitening products on the market. They claim that they are as simple as paint and go which will give you white teeth. There have been many disappointed consumers that feel that this mode of tooth whitening does not give them the results they are looking for. The main problem with these products is that they don't stay on the teeth long enough to work. This is because saliva washes the whitening products off, and lip movement tends to push off the whitening product mechanically.

SUMMARY OF THE INVENTION

The present invention relates to a device and method of whitening teeth and protecting the gums.

The present invention relates to a method for whitening teeth comprising: applying a protector under the lips (upper and lower) to protect the soft tissue and allow adequate time for a whitener to dry. It is an object of the present invention for the protector to be hydrophilic and take up to 20 times its weight in water. It is an object of the present invention for the protector to comprise latex free foam, cellulose weave, cotton woven with fibers, cotton with elastic fibers. It is an object of the present invention for the protector to comprise plastic, silicone or rubber filled with gel substance.

The method further comprises applying a tooth whitening gel to a person's teeth. It is an object of the present invention for the whitening gel to be in the form of a paint on gel that is highly adhesive and tacky, but flowable enough to penetrate the tooth to allow for oxidation/whitening process.

The system also includes a PVP based stain removal liquid with no peroxide to be used separately from the whitener to help maintain brightness during and after the whitening process is completed. This will help accelerate the whitening in that it removes stains accumulated from coffee, tea, wine, etc. The teeth are more vulnerable to stain during the whitening process. The present invention relates to a tooth bleaching gel that combines chemical stain removal with mechanical cleaning abrasives to more efficiently lift stain and "whiten" the teeth. It is an object of the present invention to freshen breath by addition of flavor compounds. Sensitivity is a frequent side effect most likely due to the chelating of calcium from the tooth structure. The main action of stain removal is from the compound (PVP) Plasdone ISP corp, NJ. These polymers are known to form a strong bond with a variety of common dyes and stains. PVP (Plasdone (ISP Corp)) is effective in removing stains from teeth and preventing restaining. The PVP forms a complex with the stain. The PVP picks up phenolics in the tooth structure which are a result of everyday use of cola, tea, wine, berries and such. The silica and or other abrasives mechanically polish the tooth surface and add to the stain removal, "whitening" of the tooth.

Hydrogen peroxide in a concentration high enough to "whiten" the teeth is controversial in safety to swallow and daily use.

The non peroxide stain removal product is comprised of the following: solvents which comprise any one of the following compounds or a mixture thereof: ethanol—most stable, water, glycerol—can cause tooth sensitivity, and propylene glycol—food grade
PVP (ISP CORP) 2% to 50%
Hydrated silica: an abrasive comprising silica, such as ZEODENT 113 (from HUBER Corporation) that is approximately 10 microns in size and with a 20% loading has an RDA of 80.
OTHER ABRASIVES: Titanium dioxide, Baking Soda, Calcium Carbonate 0.1% to 40%
Papain: Range 0.1% to 10%
Sucralose: Range 0.1 to 10%
Xylitol: Range 0.1% to 30%
Purified water
Baking Soda Range 0.1% to 40%
Flavor Mint, Vanilla mint, Citrus mint 0.1% to 20%

It is an object of the present invention for the product to remove any stain product that may adhere to the tooth by the physical silica abrasion (very gentle). It is an object of the present invention for the RDA of the product to be in the range from 80 to 110, which is less than most toothpastes. It is an object of the present invention for inorganic matter to be complexed with the PVP to be chemically removed.

It is an object of the present invention for the user to express the gel through the tube to the felt tip and use a circular rubbing motion on the tooth surface. It is an object of the present invention for the composition to be used on all tooth buccal surfaces or just on specific teeth.

It is an object of the present invention for the delivery of the two products to be as follows:

Delivery is a dual ended twist or click pen that houses the tooth whitener and stain remover in 2 separate chambers so they never mix. Both ends can have a felt tip with one hole or several holes, both ends are brushes, one end a brush, the other felt tip, or one or both ends a silicone/rubber tip or any combination of the above.

The delivery could also be a double ended lip gloss container that on chamber houses the stain remover and the other chamber houses the peroxide whitener. The applicator can have a felt "doe foot" on both ends, a brush on both ends or any combination of the above.

The fill weight of each chamber can range from approximately 1 ml to 10 ml. The material can be polypropylene, PETG, aluminum overshell, or any material that won't interfere with the stability of the active product.

The product is painted on the tooth if the applicator is a brush or doe foot. If the applicator is a felt tip on the pen, it will be rubbed against the surface of the tooth.

This is for portability of having 2 products in one and for marketing advantage.

It is an object of the present invention for the composition to be a "dual system" of stain removal in one delivery. It is an object of the present invention for the composition to polish stains by abrasion and complex/bind stains by the PVP. The process of the present invention is mechanical and chemical removal of tooth stain.

The intended instruction is to expectorate the residual product from the mouth.

It is an object of the present invention for the whitening ingredient to comprise hydrogen peroxide from about 6% to about 10%.

It is an object of the present invention for the whitening agent to comprise a remineralization agent Xylitol which acts as a sweetener and remineralizing agent.

It is an object of the present invention for the whitening agent to comprise a flavoring agent.

It is an object of the present invention for the whitening agent to comprise an adhesive to adhere to the tooth but be flowable enough to effectively whiten/oxidize the organic stains in the tooth structure.

It is an object of the present invention for the pH of the whitening agent to be between about 3.5 to 7.5.

It is an object of the present invention for the whitening agent to comprise a solvent.

It is an object of the present invention for the whitening agent to comprise a thickening agent. It is an object of the present invention for the thickening agent to be polymer PVP. It is an object of the present invention for the thickening agent to increase viscosity of bleach but not interfere with release of O2 ions from the bleach agent. PVP is a good "tackifying agent". PVP does not chemically etch the tooth. Carbomer may etch the tooth. PVP does not remove tooth enamel (Ca++ ions) by chelation. PVP does not solidify the dental bleach. It is an object of the present invention for the thickener to have a molecular weight between 90 k to 150 k (lower molecular weight PVP used more PVP needed to thicken). The thickener requires a liquid component, such as, propylene glycol, glycerin, ethanol, liquid PEG.

Other thickeners are less desirable than PVP. Carbopol has an affinity to pull Ca++ from tooth. Fumed silica dries too quickly, and is not soluble in H2O2. Natural gums are a gelatinous mess.

It is an object of the present invention for the whitening agent to be dispensed by a delivery system. It is an object of the present invention for each of the whitening agents to be delivered in a double end pen that has two chambers. The other chamber contains the PVP stain removal gel. The whitener has a brush at the end and can also be dispensed in a single brush pen. The PVP maintenance pen has a felt "doe foot" end. It is an object of the present invention for the whitening agents to be dispensed as a kit. It is an object of the present invention for each kit to have 14 days worth of upper and lower Bleach Bumpers, whitening gel and PVP maintenance gel.

It is an object of the present invention for the method to further comprise placing a gum guard/bleach bumper in a person's mouth before whitening their teeth. It is an object of the present invention for the gum guard/bleach bumper to be a barrier to gums, lips, and oral tissues from the whitener. It is an object of the present invention for the gum guard/bleach barrier to prevent "wash away" of whitener that has been a problem with paint on whiteners, which will increase effectiveness of the whitener.

It is an object of the present invention for the gum guard/bleach barrier to be compatible with the tooth whitener and not interfere with the whitening process.

It is an object of the present invention for the gum guard/bleach bumper to be flexible to allow it to conform easily to the tooth and tissue. It is an object of the present invention for the gum guard/bleach bumper to be a nonirritant to all tissues.

It is an object of the present invention for the gum guard/bleach barrier to have no sharp edges. It is an object of the present invention for the gum guard/bleach barrier to mechanically retract the lips and soft tissue away from the tooth structure during tooth whitening. It is an object of the present invention to allow a paint on whitener with a gel like viscosity to sit on the tooth for a length and period of time so that the whitener can work on the teeth. It is an object of the present invention to retract the lips enough so that the lips cannot push away the bleach.

It is an object of the present invention for the gum guard/bleach barrier to comprise a small rectangular, square, round, or oval cylinder, hollowed tube or rectangular or square shape which can be pushed under the lip, above the gum lip to retract the lips and tissue away from the teeth. It is an object of the present invention for the device to comprise a plastic, silicone, foam, fiber, cotton weave, or a gel-like consistency.

It is an object of the present invention for the diameter of the gum guard/bleach barrier to be from about 5 mm to about 20 mm. It is an object of the present invention for the device to be the length of approximately 20 mm to about 80 mm.

It is an object of the present invention for the device to be flexible enough to contour around the mouth of a user, but rigid enough to keep it's shape. It is an object of the present invention for the device not to be deformed by a small amount of saliva. It is an object of the present invention for the devices to be disposable after a single use. It is an object of the present invention for the device to be used on the upper lips or the lower lips or a combination of the two. It is an object of the present invention for the device to be placed on either the upper or lower region of the mouth.

The present invention relates to a method of applying a tooth whitening product comprising placing the device of the present invention underneath a person's lips, retracting the lips and tissue away from the teeth. A second device is placed either upper or lower. A person's front teeth are then exposed to allow a user to place a tooth whitening product on their teeth. The tooth whitening product is then allowed to dry. Once the product is dry on the teeth the devices are removed from a persons mouth and then may be disposed of.

It is an object of the present invention for the gum guard/bleach barrier to be flexible, i.e., plastic, (possibly filled with a liquid or gel like substance) that is placed under the lips and above the gum and in retraction of lips and soft tissue. So when the bleach is applied to the teeth not soft tissue comes into contact with the hydrogen peroxide. It is an object of the present invention for the gum guard to retain its shape, but still to conform to the shape of the mouth.

It is an object of the present invention for the whitening agent to have polymer resins added to the formulation to increase adhesion of actives to the teeth.

DETAILED DESCRIPTION OF THE INVENTION

In a preferred embodiment, the whitening gel comprises an additive such as hydrogen peroxide from about 6 to 10%. in an embodiment, the gel contains Xylitol.

In a preferred embodiment, a flavoring is added to the gel.

In a preferred embodiment, an adhesive is used to adhere to the tooth. The adhesive should be flowable enough to effectively whiten/oxidize the organic stains in the tooth structure.

In an embodiment the pH ranges from 3.5 to 7.5.

In an embodiment, the gel comprises a humectant possibly glycerin or a more suitable alternative. In an embodiment, a solvent is used in the gel.

In an embodiment, a thickening agent is used in the gel to increase the viscosity of bleach but not interfere with the release of O2 ions from bleach agent. In a preferred embodiment, the thickening agent is PVP. PVP is a good tackifying agent The advantages of using PVP is that is does not chemically etch the tooth (Carbomer possibly does). PVP does not remove tooth enamel (Ca++ ions) by chelation. PVP does not solidify the dental bleach. In a preferred embodiment, the molecular weight for the thickener in bleach 90 k to 150 k (lower molecular weight PVP used more PVP needed to thicken. PVP may need a liquid component (glycerin, ethanol, liquid PEG)

Other thickeners are not as useful. Carbopol has an affinity to pull Ca++ from the tooth. Fumed silica dries too quickly, and is not soluble in H2O2. Natural gums are a gelatinous mess. PEG is not used only as a thickener, H2O soluble wax.

Figure 1:
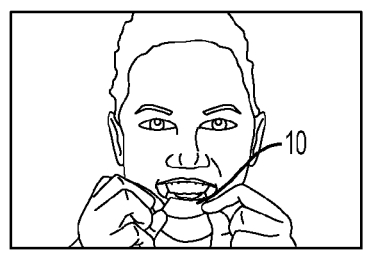
FIG. 1 shows a front view of a person holding a bleaching bumper prior to insertion under their upper lip.
Figure 2:
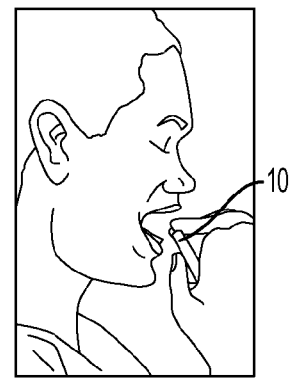
FIG. 2 shows a side view of a person holding a bleaching bumper prior to insertion under their upper lip.
Figure 3:
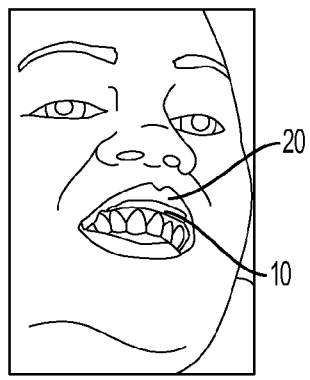
FIG. 3 shows a front view of a person having a bleaching bumper inserted under their upper lip.
Figure 4:
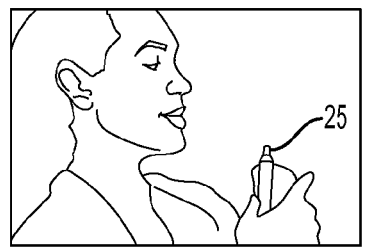
FIG. 4 shows a side view of the person in FIG. 3 prior to applying the whitening or stain removal application.
Figure 5:
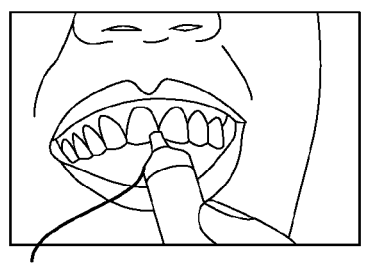
FIG. 5 shows a person having a stain removal or whitening product applied to their teeth with the bleaching bumper underneath the upper lip.
Figure 6:
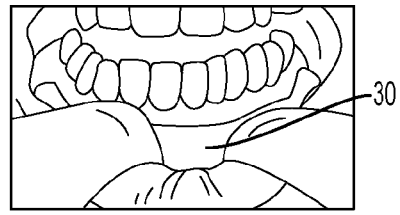
FIG. 6 shows a bleaching bumper inserted under a person's lower lip.
Figure 7:
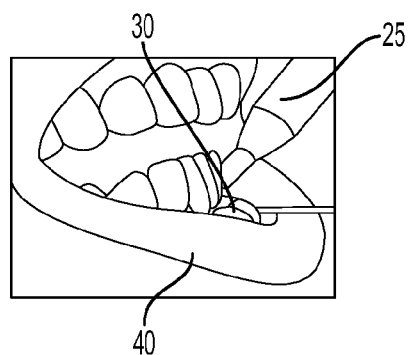
FIG. 7 shows a person applying a stain removal or whitening product to their teeth while the bleaching bumper is underneath.

FIGS. 1-7 show a user using the bleaching bumpers and a whitener of the present invention. A bleaching bumper 10 is placed under the upper lip 20. A whitening product 25 is then placed on the teeth. Once the whitener is dry, the bleaching bumper 10 is removed. FIG. 6 shows a bleaching bumper 30 placed under the lower lip 40 and the whitener 25 being placed on the teeth.

The invention claimed is:

1. A personal use kit for whitening and maintaining a persons teeth comprising: upper and lower bleaching bumpers which take up to 20 times their weight in water, a whitening paint-on gel; and a PVP paint-on maintenance gel containing no peroxide.

2. A kit according to claim 1, wherein said upper and lower bleaching bumpers comprise: a rectangular, square, round, oval shape, or a hollowed tube which is pushed under the lip, above the gum lips and retracts the lips and tissue away from the teeth.

3. A kit according to claim 1, wherein said upper and lower bleaching bumpers are made of plastic, silicone, foam, or fiber.

4. A kit according to claim 1, wherein said upper and lower bleaching bumpers have a diameter of from 5 mm to 20 mm.

5. A kit according to claim 1 wherein said upper and lower bleaching bumpers comprise a rectangular, square, round, oval shape, a cylinder or a hollowed tube.

6. A kit according to claim 5 wherein said upper and lower bleaching bumpers comprise latex-free foam, cellulose weave, cotton woven with fibers, or cotton with elastic fibers.

7. A kit according to claim 1, wherein said whitening gel comprises a paint-on gel that is adhesive and tacky, but flowable enough to penetrate a tooth to allow for oxidation/whitening; and said PVP paint-on drying maintenance gel comprises a PVP stain removal gel with no peroxide used separately from said whitening gel and after said whitening process is completed.

8. A kit according to claim 7, wherein said PVP paint-on maintenance gel combines chemical stain removal with mechanical cleaning abrasives to lift stain and whiten teeth.

9. A kit according to claim 7 wherein said PVP is 2 weight % to 50 weight % of said stain removal gel.

* * * * *